(12) United States Patent
Kottkamp

(10) Patent No.: US 8,685,345 B2
(45) Date of Patent: Apr. 1, 2014

(54) INSERT FOR A SAMPLE CHAMBER OF A MULTI-WELL PLATE

(75) Inventor: Eike Kottkamp, Lubbecke (DE)

(73) Assignee: Erwin Quarder Systemtechnik GmbH, Espelkamp (DE)

( * ) Notice: Subject to any disclaimer, the term of this patent is extended or adjusted under 35 U.S.C. 154(b) by 0 days.

(21) Appl. No.: 13/589,504

(22) Filed: Aug. 20, 2012

(65) Prior Publication Data

US 2013/0052102 A1   Feb. 28, 2013

(30) Foreign Application Priority Data

Aug. 22, 2011   (DE) .................. 10 2011 110 782

(51) Int. Cl.
| | | |
|---|---|---|
| *G01N 31/16* | (2006.01) | |
| *B01L 3/00* | (2006.01) | |
| *B01L 99/00* | (2010.01) | |
| *C12M 1/22* | (2006.01) | |
| *C12M 3/00* | (2006.01) | |
| *C12M 1/34* | (2006.01) | |
| *C12M 1/12* | (2006.01) | |

(52) U.S. Cl.
USPC ........... 422/552; 422/568; 422/569; 422/570; 435/288.4; 435/297.5; 435/305.3

(58) Field of Classification Search
USPC ............ 422/552, 568–570; 435/297.5, 305.3, 435/288.4
See application file for complete search history.

(56) References Cited

U.S. PATENT DOCUMENTS

| | | | | |
|---|---|---|---|---|
| 5,139,951 | A | * | 8/1992 | Butz et al. ................ 435/297.5 |
| 2003/0162285 | A1 | * | 8/2003 | Tajima ..................... 435/287.2 |
| 2005/0226786 | A1 | | 10/2005 | Hager |
| 2011/0014673 | A1 | | 1/2011 | Hukari |

FOREIGN PATENT DOCUMENTS

| | | |
|---|---|---|
| DE | 10150269 A1 | 6/2003 |
| DE | 102008031265 A1 | 1/2010 |
| DE | 102008035644 A1 | 2/2010 |
| EP | 1391242 A2 | 2/2004 |
| WO | 2007120515 A1 | 10/2007 |

OTHER PUBLICATIONS

Deutsches Patent- unf Markenamt (German Patent and Trademark Office), Search Report, Mar. 13, 2012.
Brischwein, M., Chip statt Maus: Microsensorarrays zur Chemikalienprufung, In: Nachr. Chem., vol. 54, 2006, Nr. 2, S. 115-120.

(Continued)

*Primary Examiner* — Jill Warden
*Assistant Examiner* — Julie Tavares
(74) *Attorney, Agent, or Firm* — Laurence P. Colton; Smith Risley Tempel Santos LLC

(57) ABSTRACT

An insert for a sample chamber of a multi-well plate, which delimits the sample chamber upwardly, so as to form a measurement space, when the insert is in the state in which it is fitted into the sample chamber. The insert has at least two portions with outer contours differing from one another, one of the portions being a sealing portion with a continuous sealing surface, which sealing portion is adapted to a corresponding, in particular hollow-cylindrical sealing portion, with a likewise continuous sealing surface, of the sample chamber, in such a way that the insert sealing portion and the sample chamber sealing portion can be connected to one another releasably and in a liquid-tight manner by means of a press fit.

9 Claims, 2 Drawing Sheets

(56) References Cited

OTHER PUBLICATIONS

Brischwein, M., Moglichkeiten und Grenzen der Mikrosensortechnologie in zellularer Diagnosti, und Pharmascreening, In: Chemie Ingenieur Technik, vol. 77, 2005, Nr. 12, S. 55-59.

Lob, V., Cell-based Assays: Mikrosensorarray-basiertes Screening an lebenden Zellen und Geweben, In: BIOspektrum, vol. 11, 2005, Sonderheft Chiptechnologie & RNA in Forschung und Anwendung, S. 511-512.

* cited by examiner

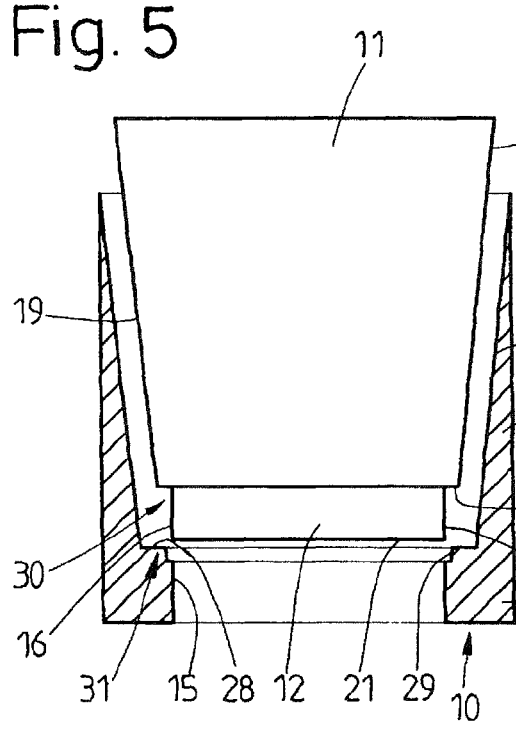
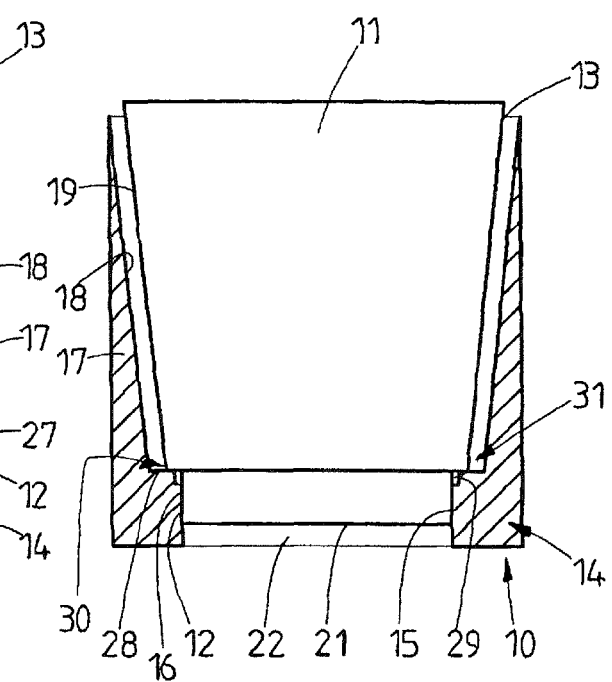

INSERT FOR A SAMPLE CHAMBER OF A MULTI-WELL PLATE

STATEMENT OF RELATED APPLICATIONS

This patent application claims the benefit and priority under 35 USC 119 of German Patent Application No. 10 2011 110 782.0 having a filing date of 22 Aug. 2011.

BACKGROUND OF THE INVENTION

1. Technical Field

The present invention relates to an insert for a sample chamber of a multi-well plate, which delimits the sample chamber upwardly, so as to form a measurement space, when the insert is in the state in which it is fitted into the sample chamber. The invention relates, furthermore, to a multi-well plate having a plurality of sample chambers, such an insert being capable of being fitted into at least one sample chamber.

2. Prior Art

Multi-well plates are known as standard sample vessels. They serve for the reception and investigation of the most diverse possible sample types, such as, for example, biological cell samples. Individual sample chambers or wells are arranged, as a rule, in the form of a matrix on such a plate. The multi-well plates are usually covered upwardly with flat lids.

However, inserts which are designed as stoppers and which are inserted into the sample chambers from above by hand have also become known. In this case, a measurement space, in which the sample to be investigated is arranged, is formed between the lower end of the insert and that region of the sample chamber which is arranged below it.

The measurement space is usually filled with a fluid component which, for example, can supply nutrients to a biological sample. Further, specific active substances can be added to the sample via such a fluid component.

In this context, multi-well plates are also known in which the fluid component flows through the sample chamber which forms part of a multi-chamber system. Such a multi-chamber system is disclosed, inter alia, in DE 10 2008 035 644 A1.

In the systems known in the prior art and composed of multi-well plates and of associated sample chamber inserts, the lack of sealing between the sample chamber and the insert presents a problem. On account of this, after the insert has been fitted, the fluid component may escape from the measurement space into the upper region of the sample chamber in an undesirable way.

In DE 10 2008 035 644 A1, the insert disclosed there may easily execute up-and-down movements in the sample chamber. On account of this, and also, in general, as a consequence of the form of construction, in DE 10 2008 035 644 A1 the insert is at best seated in the sample chamber with approximate sealing, as is explicitly referred to. The leaks mentioned may therefore occur. Such a leak leads to deviations in the actual fluid flow flowing through the measurement space from the theoretical or desired flow.

BRIEF SUMMARY OF THE INVENTION

The object of the present invention is to develop further the insert and the multi-well plate of the type mentioned in the introduction, particularly with regard to sealing between the insert and sample chamber.

This object is achieved by means of an insert for a sample chamber of a multi-well plate, which delimits the sample chamber upwardly, so as to form a measurement space, when the insert is in the state in which it is fitted into the sample chamber, characterized in that the insert has at least two portions with outer contours differing from one another, one of the portions being a sealing portion with a continuous sealing surface, which sealing portion is adapted to a corresponding, in particular hollow-cylindrical sealing portion, with a likewise continuous sealing surface, of the sample chamber, in such a way that the insert sealing portion and the sample chamber sealing portion can be connected to one another releasably and in a liquid-tight manner by means of a press fit.

This object also is achieved by means of a multi-well plate having a plurality of sample chambers, an insert being capable of being fitted into at least one sample chamber, in particular an insert as disclosed above and herein, which delimits the sample chamber upwardly, so as to form a measurement space, when the insert is in the state in which it is fitted into the sample chamber, characterized in that the sample chamber has an, in particular, hollow-cylindrical sample chamber sealing portion with a continuous sealing surface, which sample chamber sealing portion is adapted to a corresponding sealing portion of the insert with a likewise continuous sealing surface, in such a way that the insert sealing portion and the sample chamber sealing portion can be connected to one another releasably and in a liquid-tight manner by means of a press fit.

This object also is achieved by means of a system composed of a multi-well plate having a plurality of sample chambers as disclosed above and herein and with at least one insert as disclosed above and herein.

The insert according to the invention accordingly has at least two portions preferably connected in one piece and with outer contours differing from one another, one of the portions being a preferably cylindrical sealing portion with a continuous sealing surface, which sealing portion is adapted to a corresponding, in particular hollow-cylindrical sealing portion, with a likewise continuous sealing surface, of the sample chamber or well, in such a way that the insert sealing portion and the sample chamber sealing portion can be connected to one another or, when the insert is in the fitted-in state, are connected to one another releasably and in a liquid-tight manner by means of a press fit.

In other words, both the insert and the bowl-like or vessel-like sample chamber have in each case sealing portions matching with one another. The press fit is achieved in that the insert sealing portion has oversize with respect to the sample chamber sealing portion surrounding it in the fitted-in state or in that the insert sealing portion is closed or pressed with oversize into the sample chamber sealing portion from above.

Tests by the applicant showed that, in the case of the common fluid components used in connection with multi-well plate systems, such a press fit makes it possible to have especially good and permanent sealing between the insert and sample chamber. At the same time, a suitable choice of the parameters of the press fit (degree of oversize, axial dimensions of the sealing portions or of the sealing surfaces, etc.) can ensure the releasability of the press fit or the respective insert from the sample chamber.

As a rule, a plurality of inserts according to the invention will be necessary for a multi-well plate. These can be connected to one another via connecting webs and form a lid part for the multi-well plate.

The insert and/or the lid part for the multi-well plate on which a plurality of such inserts is arranged are/is preferably produced as an injection moulding from plastic.

Additionally or alternatively, the sample chamber and/or the entire multi-well plate having the plurality of sample chambers may be produced as a plastic injection moulding.

In a further form of the invention, the further insert portion differing in outer contour from the sealing portion advantageously runs, in the fitted-in state, obliquely upwards and widens upwardly. This obliquely running portion then forms, within the framework of the injection-moulding method, a mould removal slope for the simple removal of the insert from the mould.

The oblique portion of the insert is in this case preferably designed conically.

In an especially preferred embodiment of the invention, the insert consists of exactly two portions differing from one another, to be precise, on the one hand, of the preferably cylindrical sealing portion of the insert and, on the other hand, of the, in particular, conical insert portion adjoining the latter at the top and widening obliquely upwards. Alternatively, however, additional portions could also be provided.

As regards the sealing portion of the insert, this preferably forms the lower free end of the insert. However, this is not mandatory.

The outer contour of the insert sealing portion and the outer contour of the obliquely running insert portion may adjoin one another continuously, that is to say without any offset. Alternatively, the outer contour of the insert sealing portion and the outer contour of the obliquely running insert portion may, however, also adjoin one another discontinuously, that is to say with offset. In this case, the outside diameter of the insert sealing portion in the joining region would be smaller than the outside diameter of the obliquely running portion.

As regards the sample chamber of the multi-well plate, its sample chamber sealing portion is preferably designed hollow-cylindrically with a continuous sealing surface. The sealing surface is accordingly formed by the continuous inner surface of the hollow-cylindrical portion. The inside diameter of the hollow-cylindrical sealing portion is in this case naturally smaller than the outside diameter of the matching sealing portion of the insert in order to make the press fit possible.

Further, there may be provision whereby the sample chamber has an, in particular, horizontally running, in particular horizontal or radial stop, arranged preferably above the sample chamber sealing portion, for limiting the depth of penetration of the insert into the sample chamber. The insert butts against this stop from above when it is being fitted into the sample chamber.

In one embodiment, the stop of the sample chamber may be radially contiguous on the outside to the insert portion running obliquely upwards.

Further, there may be provision whereby a continuous clearance is arranged in the sample chamber between the stop and the sample chamber sealing portion, so as to form a step between the stop and sample chamber sealing portion. This clearance is in this case preferably designed in such a way that, if appropriate, the fluid which is arranged in the measurement space can form on or in this clearance meniscuses which assist sealing between the sample chamber sealing portion and the insert sealing portion.

The above-described butting of the insert against the sample chamber stop requires a corresponding insert stop butting against this sample chamber stop.

Insofar as the outer contour of the insert sealing portion and the outer contour of the obliquely running insert portion adjoin one another with offset in the way described above, so that the outside diameter of the insert sealing portion in the joining region is smaller than the outside diameter of the obliquely running portion, the insert stop is preferably formed by the margin, resulting from this and projecting with respect to the insert sealing portion, of the further, oblique insert portion.

Alternatively, the insert may also have in its upper region, preferably at its upper free end, a preferably continuous, in particular horizontal or radial stop which, in the fitted-in state, butts against the free upper margin of the sample chamber. The free upper margin of the sample chamber in this case forms the sample chamber stop.

As a rule, the insert is designed to be essentially or completely rotationally symmetrical about its longitudinal mid-axis. Noses, projections or grooves may in this case be provided in order to make it possible to have a preferential orientation of the insert in the sample chamber.

BRIEF DESCRIPTION OF THE DRAWINGS

Further features of the present invention may be gathered from the accompanying patent claims, the following description of preferred exemplary embodiments of the invention and the accompanying drawings in which:

FIG. 5 shows a cross-sectional view of a further embodiment of an insert in a state corresponding to FIG. 1.

FIG. 6 shows the view from FIG. 5 with the insert fitted into the sample chamber and ensuring sealing.

DETAILED DESCRIPTION OF PREFERRED EMBODIMENTS

Figure 1:
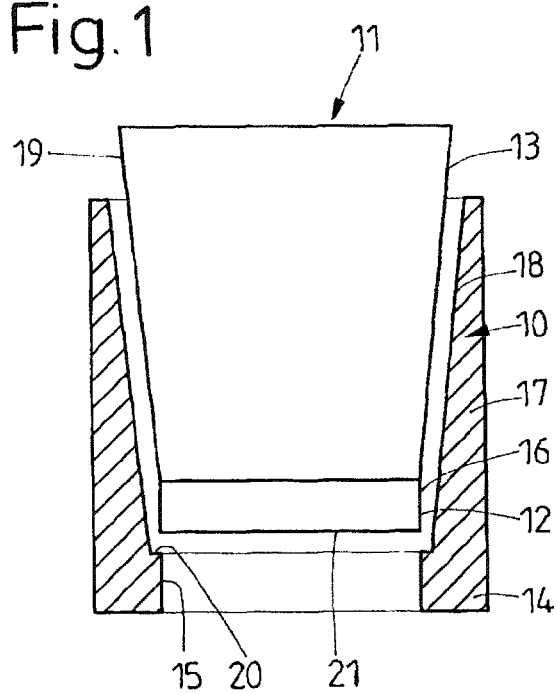
FIG. 1 shows a cross-sectional view of an insert penetrating into a sample chamber of a multi-well plate, in a state in which the insert is not yet fitted (sealingly) into the sample chamber.

FIGS. 1-6 show in each case simply different embodiments of a detail of a system composed of a multi-well plate and of associated inserts, to be precise different embodiments of an individual well 10 or of an individual sample chamber 10 of a multi-well plate, otherwise not illustrated, and of an insert 11 associated with or adapted to the latter.

Such a multi-well plate usually has a multiplicity of bowl-like or vessel-like upwardly open sample chambers distributed on a plate in a grid-like or matrix-like manner and extending upwards.

The multi-well plates of the present exemplary embodiments are what is known as a three-chamber system. The or each of the sample chambers 10, only detail of which is illustrated, is assigned in each case a separate inflow chamber and a separate outflow chamber. The inflow chamber, sample chamber and outflow chamber are connected to one another in their lower region via one or more connecting ducts. The inflow and outflow chambers and also the connecting ducts are not illustrated in the drawing.

The insert 11, when in the state fitted into the sample chamber 10 (FIGS. 2, 4 and 6), that is to say in a final state, forms, together with the sample chamber 10, a measurement space 22, only detail of which is illustrated, in which the usually biological sample to be investigated is arranged.

To investigate the sample, a suitable fluid is imparted into the inflow chamber and flows through the inflow chamber along the connecting ducts into the measurement space 22 and from there into the outflow chamber, until the fluid columns in the chambers are equalized. A fluid flow is thereby induced in the measurement space 22. The fluid therefore flows along the sample. For example, when body cells are being investigated, flow conditions prevailing in the body can in this case be simulated.

The observation of the samples may take place visually, for example in that the bottom of the sample is made transparent. As a rule, however, the monitoring of the samples takes place in an automated way by means of sensor chips, in particular biosensor chips, assigned to the sample chambers of the multi-well plate.

Sealing between the insert 11 and the sample chamber 10 is particularly essential.

Figure 2:
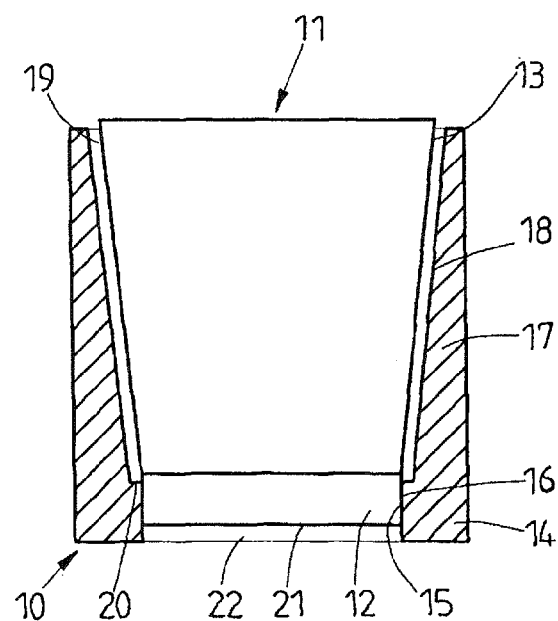
FIG. 2 shows the view from FIG. 1 with the insert fitted into the sample chamber, so that the insert is seated sealingly in the sample chamber.

The insert 11 shown in FIGS. 1 and 2, which is rotationally symmetrical about its longitudinal mid-axis, has a lower sealing portion 12 and a conical portion 13 contiguous to the latter at the top. The insert sealing portion 12 is designed cylindrically. The insert 11 may in this case be of solid form or be formed entirely or in parts as a hollow body. It is a plastic injection moulding produced by an injection-moulding method.

The conical portion 13 forms suitable mould removal slopes which in the production process enable the cast injection moulding to be removed from the mould in a simple way or enable the injection moulding to be extracted easily from the injection mould.

The axial or vertical dimensions of the cylindrical sealing portion 12 are kept sufficiently small to assist the easy removal of the insert 11 from the mould.

The insert 11 is adapted to the sample chamber 10 of the multi-well plate.

The sample chamber 10, likewise rotationally symmetrical about its longitudinal axis, has a lower hollows-cylindrical sealing portion 14 with a continuous vertical sealing surface 15 pointing inwards.

The terms "vertical" and "horizontal" refer in the context of this application to a conventional arrangement of the multi-well plate on a horizontal surface, for example a table.

When the insert 11 is in the state fitted into the sample chamber 10 (FIG. 2), the continuous sealing surface 16 of the cylindrical sealing portion 12, that is to say the vertical outside of the cylinder, bears sealingly against the continuous sealing surface 15, assigned to it, of the hollow-cylindrical sealing portion 14 of the sample chamber 10.

The sealing action is in this case achieved by means of a press fit. For this purpose, the outside diameter of the sealing portion 12 is larger by a certain amount than the inside diameter of the hollow-cylindrical sealing portion 14. The insert 11 is therefore pressed, for sealing purposes, with oversize into the free space surrounded by the hollow-cylindrical sealing portion 14.

Above the sealing portion 14, the sample chamber 10 widens upwards. Widening is achieved in that a hollow-body portion 17 of the insert 11 with an inside or inner surface 18 running obliquely, in the present case conically, is arranged above the hollow-cylindrical sealing portion 14 so as to be connected in one piece to the latter.

The inclination of the inner surface 18 of the hollow-body portion 17 of the sample chamber 10 is adapted to the inclination of the conical portion 13 of the insert 11. In the present exemplary embodiment, the outer surface 19 of the conical portion 13 of the insert 11 and the inside or inner surface 18 of the hollow-body portion 17 run essentially parallel to one another in the fitted-in state of the insert 11.

The sample chamber 10 or the entire multi-well plate with the multiplicity of sample chambers 10 is likewise in the present exemplary embodiment an injection moulding made from plastic. The individual portions 14, 17 of the sample chamber 10 are accordingly connected to one another in one piece.

The sealing surface 15 of the sealing portion 14 of the sample chamber 10 is connected to the inner surface 18 of the hollow-body portion 17 via a radial or horizontal step 20.

The insert 11, in the present case the sealing portion 12 thereof, has a closed underside 21 which is contiguous to the measurement space 22. In the fitted-in state of the insert 11, the measurement space 22 is formed essentially by this underside 21, and also by the regions of the sample chamber 10 which are arranged below the insert 11, in particular the corresponding wall portion, arranged in the lower region, of the sample chamber 10, and by a bottom wall usually running horizontally.

Figure 3:
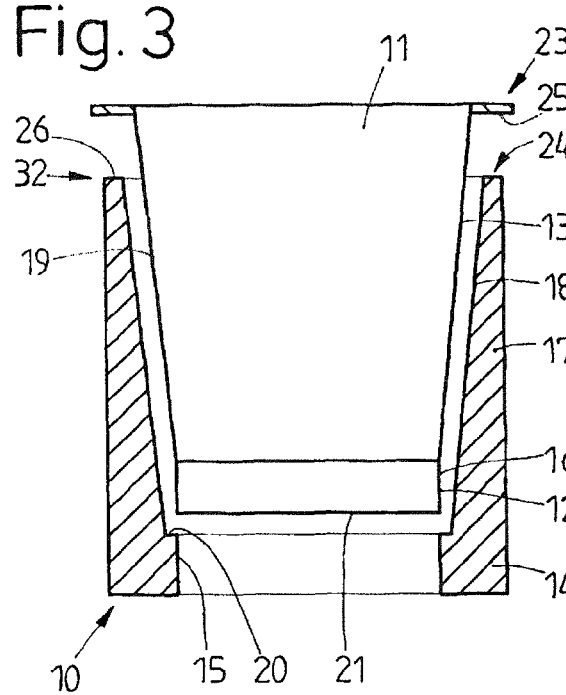
FIG. 3 shows a cross-sectional view of a further embodiment of an insert in a state corresponding to FIG. 1.
Figure 4:
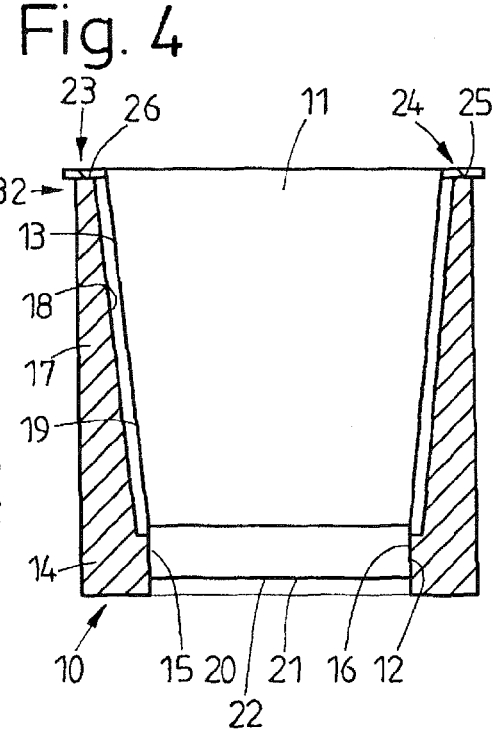
FIG. 4 shows the view from FIG. 3 with the insert fitted into the sample chamber and ensuring sealing.

The embodiment of FIGS. 3 and 4 differs from the embodiment of FIGS. 1 and 2 in a stop 23 of the insert 11, the said stop being arranged at the upper margin of the latter. This stop 23 limits the depth of penetration of the insert 11 into the sample chamber 10 during the fitting-in operation. The stop 23 butts at the end of the fitting-in operation against the upper horizontal continuous margin 24 of the sample chamber 10, the said margin in this case forming a corresponding counterstop 32. The stop 23 of the insert 11 is designed as a continuous stop ring running radially or horizontally, with a lower stop-ring surface 25 which, in the fitted-in state, bears against or lies on top an upper likewise horizontal ring surface 26 of the stop 32 of the sample chamber 10.

FIGS. 5 and 6 show a further embodiment of the invention. In the case of the insert 11 illustrated there, the sealing portion 12 is set back with respect to the conical portion 13. More specifically, the sealing portion 12 forms a cylindrical extension which is arranged coaxially to the conical portion 13 and of which the outside diameter in the region joined to the conical portion 11 is smaller than the outside diameter of the conical portion 11.

In other words, the smallest outside diameter, defined by the lower end of the conical portion 11, of the conical portion 11 is larger than the outside diameter of the sealing portion 12. The outer contour of the insert 11 therefore makes a jump, that is to say it runs discontinuously, in the transitional or joining region between the sealing portion 12 and conical portion 13.

In this case, the margin 27, projecting with respect to the cylindrical sealing portion 12, of the underside of the conical portion 13 forms a stop 30 of the insert 11, the said stop butting against a horizontal or radial ring surface 28 of a stop 31 of the sample chamber 10 when the insert 11 is fitted into the sample chamber 10 from above. The depth of penetration of the insert 11 in the direction of the sample-chamber bottom is correspondingly limited.

In this embodiment, furthermore, there is provision whereby a continuous clearance 29 is arranged between the stop 31 of the sample chamber 10 and the sample chamber sealing portion 14 so as to form a step between the stop 31 and sample chamber sealing portion 14. The dimensions of the clearance 29 are selected in such a way that fluid possibly flowing between the sealing surfaces 15, 16 can form in the region of the clearance 29 one or more meniscuses preventing the fluid from flowing through the sealing surfaces 15, 16 any further.

As a person skilled in the art will recognize, the present invention is not restricted to multi-well plates with three-chamber systems or to inserts for such three-chamber systems.

Even in the case of single-chamber systems, it may be necessary to seal off the corresponding insert with respect to the sample chamber in the way described.

The same applies in a similar way to solutions in which the multi-well plate does not have the inflow and outflow chambers, but instead the inserts have cavities which in each case form the inflow and the outflow chambers. The fluid component arranged in the inflow chamber of the respective insert in this case emerges from an orifice at the bottom of the insert to form the fluid flow, penetrates into the measurement space formed by the insert, on the one hand, and the sample chamber of the multi-well plate, on the other hand, and then flows via a corresponding further orifice at the bottom of the insert into the outflow chamber of the latter. Even in inserts of this type, the sealing according to the invention of the insert with respect to the sample chamber can be used.

LIST OF REFERENCE SYMBOLS

10 Sample chamber
11 Insert
12 Sealing portion
13 Conical portion
14 Sealing portion
15 Sealing surface
16 Sealing surface
17 Hollow-body portion
18 Inner surface
19 Outer surface
20 Step
21 Underside
22 Measurement space
23 Stop
24 Upper margin
25 Stop-ring surface
26 Upper ring surface
27 Margin
28 Ring surface
29 Clearance
30 Stop
31 Stop
32 Stop

What is claimed is:

1. A multi-well plate having:
a plurality of sample chambers (10), and
an insert (11) that is fitted into at least one of the sample chambers (10) and which delimits the sample chamber (10) upwardly, so as to form a measurement space (22), when the insert (11) is in a state in which the insert (11) is fitted into the sample chamber (10),
wherein the sample chamber (10) has:
a hollow-cylindrical sample chamber sealing portion (14) with a continuous sealing surface (15), which sample chamber sealing portion (14) is adapted to a corresponding insert sealing portion (12) of the insert (11) with a likewise continuous sealing surface (16), in such a way that the insert sealing portion (12) and the sample chamber sealing portion (14) are connected to one another releasably and in a liquid-tight manner by means of a press fit;
a stop (31) for the insert (11) for limiting the depth of penetration of the insert (11) into the sample chamber (10), against which stop (31) the insert (11) butts from above when being fitted into the sample chamber (10); and
a continuous clearance (29) located between the stop (31) and the sample chamber sealing portion (14), the continuous clearance (29) forming a step between the stop (31) and the sample chamber sealing portion (14), which step is designed in such a way that fluid that is arranged in the measurement space (22) forms meniscuses on or in the continuous clearance (29) that assist in forming a seal between the sample chamber sealing portion (14) and the insert sealing portion (12).

2. The multi-well plate according to claim 1, wherein the sample chamber (10) further comprises, above the hollow-cylindrical sample chamber sealing portion (14), an obliquely running portion (17) that widens upwards and opposite which lies, in the fitted-in state of the insert (11), an insert portion (13) adapted to the obliquely running portion (17) and running, at least in regions, parallel to the obliquely running portion (17).

3. The multi-well plate according to claim 2, wherein the stop (31) is horizontally running.

4. The multi-well plate according to claim 2, wherein the stop (31) is arranged above the sample chamber sealing portion (14).

5. The multi-well plate according to claim 3, wherein the stop (31) is arranged above the sample chamber sealing portion (14).

6. The multi-well plate according to claim 2, wherein the stop (31) is radially contiguous on the outside to the obliquely running portion (17).

7. The multi-well plate according to claim 3, wherein the stop (31) is radially contiguous on the outside to the obliquely running portion (17).

8. The multi-well plate according to claim 4, wherein the stop (31) is radially contiguous on the outside to the obliquely running portion (17).

9. The multi-well plate according to claim 5, wherein the stop (31) is radially contiguous on the outside to the obliquely running portion (17).

* * * * *